United States Patent [19]
Lambowitz et al.

[11] Patent Number: 5,804,418
[45] Date of Patent: Sep. 8, 1998

[54] METHODS FOR PREPARING NUCLEOTIDE INTEGRASES

[75] Inventors: Alan Marc Lambowitz; Georg Mohr; Roland Saldanha; Manabu Matsuura, all of Columbus, Ohio

[73] Assignee: The Ohio State University Research Foundation, Columbus, Ohio

[21] Appl. No.: 752,238

[22] Filed: Nov. 19, 1996

[51] Int. Cl.$^6$ .............................. C12P 21/02; C12P 19/34; C12N 9/12; C12N 15/54

[52] U.S. Cl. ..................... 435/69.1; 435/194; 435/91.1; 536/23.2; 536/23.4; 536/24.1

[58] Field of Search .................................. 435/194, 69.1, 435/91.1; 536/23.2, 23.4, 24.1

[56] References Cited

U.S. PATENT DOCUMENTS 5,498,531   3/1996   Jarrell ...................................... 435/93.1

OTHER PUBLICATIONS

"Group I and group II introns" by Saldanha, et al. *The FASEB Journal*, vol 7, Jan. 1993, pp. 15–24.

"Group II Intron Mobility Occurs to Target DNA–Primed Reverse Transcription" by Zimmerly, et al. *Cell*, vol. 82, Aug. 25, 1995, pp. 545–554.

"An Expanding Universe of Introns" by Belfort *Science*, vol. 262, Nov. 12, 1993, pp. 1009–1010.

"Integration of Group II Intron bI1 into a Foreign RNA by Reversal of the Self–Splicing Reaction In Vitro" by Mörl and Schmelzer *Cell*, vol. 60, Feb. 23, 1990, pp. 629–636.

"A Group II Intron RNA is a Catalytic Component of a DNA Endonuclease Involved in Intron Mobility" by Zimmerly, et al., *Cell*, vol. 83, Nov. 17, 1995, pp. 1–10.

"RNA enzymes (ribozymes) as antiviral therapeutic agents" by Rossi and Sarver *Tibtech* vol. 8, Jul. 1990, pp. 179–183.

"Mobile Group II Introns of Yeast Mitochondrial DNA Are Novel Site Specific Retroelements" by Moran, et al., *Molecular and Cellular Biology*, vol. 15, No. 5, May 1995, pp. 2828–2838.

"Evolutionary relationships amoung group II Intron–encoded proteins and indentification of a conserved domain that may be related to maturase function" by Mohr, et al., *Nucleic Acids Research* vol. 21, No. 22, 1993, pp. 4991–4997.

"Reverse Transcriptase Activity Associated with Maturase–Encoding Group II Introns In Yeast Mitochondria" by Kennell, et al., *Cell*, vol., 73, Apr. 9, 1993, pp. 133–146.

"Introns as Mobile Genetic Elements" by Lambowitz, et al., *Annual Reviews Biochem.*, vol. 62, pp. 587–622, 1993.

"Efficient integration of an intron RNA into double–stranded DNA by reverse splicing" by Yang, et al., *Nature,* vol. 381, Mya 1996, pp. 332–335.

"Splicing of Group II intron involved in the conjugative transfer of pRS01 in Lactococci" by Mills, et al., *J. of Bacteriology*, vol. 178, Jun. 1996, pp. 3531–3538.

"Splicing of a group II intron in a functional transfer gene of *Lactococcus lactis*" by Shearman, et al., *Molecular Microbiology*, vol. 21, Jul. 1996, pp. 45–53.

"Mobility of Yeast Mitochondrial Group II Introns: Engineering a New Site Specificity and Retrohoming via full reverse splicing" by Eskes, et al., *Cell* (in press), May 1997.

*Primary Examiner*—Keith D. Hendricks
*Attorney, Agent, or Firm*—Calfee, Halter & Griswold LLP

[57] ABSTRACT

The present invention provides new, improved, and easily manipulable methods for making nucleotide integrases. In one embodiment, the nucleotide integrase is prepared by introducing a DNA molecule which comprises a group II intron DNA sequence into a host cell. The group II intron DNA sequence is then expressed in the host cell such that RNP particles having nucleotide integrase activity are formed in the cell. Such RNP particles comprise an exiced group II intron RNA encoded by the introduced DNA molecule and a group II intron-encoded protein encoded by the introduced DNA molecule. Thereafter, the nucleotide integrase is isolated from the cell. In another embodiment, the nucleotide integrase is prepared by combining in vitro an excised, group II intron RNA, referred to hereinafter as "exogenous RNA", with a group II intron-encoded protein. In another embodiment, the nucleotide integrase is prepared by combining in vitro an excised, group II intron RNA, referred to hereinafter as "exogenous RNA", with an RNA-protein complex which comprises a group II intron-encoded protein. Preferably, the exogenous RNA is prepared by in vitro transcription of a DNA molecule which comprises the group II intron sequence. Preferably, the group II intron-encoded protein is made by introducing into a host cell a DNA molecule which comprises the open reading frame sequence of a group II intron, and then expressing the the open reading sequence in the host cell such that the group II intron-encoded protein encoded by the open reading frame sequence is formed in the cell. Preferably, the RNA-protein complex is made by introducing into a host cell a DNA molecule comprising a group II intron DNA sequence which encodes a splicing-defective group II intron RNA. The present invention also relates to a nucleotide integrase and an improved method for making RNA-protein complexes for use in preparing nucleotide integrases in vitro.

19 Claims, 7 Drawing Sheets

Fig. 2

```
         10         20         30         40         50         60         70         80         90
aagcttAGAG AAAAATAATG CGGTGCTTGG TCATCACCTC ATCCAATCAT TTTCTCCTGA TGACAATCTA ACTCCTGAAC AAATTCATGA 100        110        120        130        140        150        160        170        180
AATAGGTCGT CAAACCATAT TAGAATTTAC AGGTGGCGAA TATGAATTTG TGATTGCAAC CCACGTCGAT CGTGAACACA TCCATAACGT 190        200        210        220        230        240        250        260        270
GCGCCCAGAT AGGGTGTTAA GTCAAGTAGT TTAAGGTACT ACTCTGTAAG ATAACACAGA AAACAGCCAA CCTAACCGAA AAGCGAAAGC 280        290        300        310        320        330        340        350        360
TGATACGGGA ACAGAGCACG GTTGGAAAGC GATGAGTTAC CTAAAGACAA TCGGCTACGA CTGAGTCGCA ATGTTAATCA GATATAAGGT 370        380        390        400        410        420        430        440        450
ATAAGTTGTG TTTACTGAAC GCAAGTTTCT AATTTCGGTT ATGTGTCGAT AGAGGAAAGT GTCTGAAACC TCTAGTACAA AGAAAGGTAA 460        470        480        490        500        510        520        530        540
GTTATGGTTG TGGACTTATC TGTTATCACC ACATTTGTAC AATCTGTAGG AGAACCTATG GAACGAAAC GAAAGCGATG CCGAGAATCT 550        560        570        580        590        600        610        620        630
GAATTTACCA AGACTTAACA CTAACTGGGG ATACCCTAAA CAAGAATGCC TAATAGAAAG GAGGAAAAAG CTATAGCAC TAGAGCTTGA 640        650        660        670        680        690        700        710        720
AAATCTTGCA AGGGTACGGA GTACTCGTAG TAGTCTGAGA AGGGTAACGC CCTTTACATG GCAAGGGGT ACAGTTATTG TGTACTAAAA 730        740        750        760        770        780        790        800        810
TTAAAAATTG ATTAGGGAGG AAAACCTCAA AATGAAACCA ACAATGGCAA TTTTAGAAAG AATCAGTAAA AATTCACAAG AAAATATAGA
                                            M  K  P     T  M  A  I  L  E  R     I  S  K  N  S  Q  E    N  I  D 820        830        840        850        860        870        880        890        900
CGAAGTTTTT ACAAGACTTT ATCGTTATCT TTTACGTCCA GATATTTATT ACGTGGCGTA TCAAAATTTA TATTCCAATA AAGGAGCTTC
 E  V  F    T  R  L  Y    R  Y  L    L  P  P    D  I  Y  Y    V  A  Y    Q  N  L    Y  S  N  K    G  A  S 910        920        930        940        950        960        970        980        990
CACAAAAGGA ATATTAGATG ATACAGCGGA TGGCTTTAGT GAAGAAAAAA TAAAAAAGAT TATTCAATCT TTAAAAGACG GAACTTACTA
 T  K  G    I  L  D  D    T  A  D    G  F  S    E  E  K  I    K  K  I    Q  S  L    K  D  G    T  Y  Y 1000       1010       1020       1030       1040       1050       1060       1070       1080
TCCTCAACCT GTACGAAGAA TGTATATTGC AAAAAAGAAT TCTAAAAAGA TGAGACCTTT AGGAATTCCA ACTTTCACAG ATAAATTGAT
 P  Q  P    V  R  R  M    Y  I  A    K  K  N    S  K  K  M    R  P  L    G  I  P    T  F  T  D    K  L  I 1090       1100       1110       1120       1130       1140       1150       1160       1170
CCAAGAAGCT GTGAGAATAA TTCTTGAATC TATCTATGAA CCGGTATTCG AAGATGTGTC TCACGGTTTT AGACCTCAAC GAAGCTGTCA
 Q  E  A    V  R  I  I    L  E  S    I  Y  E    P  V  F  E    D  V  S    H  G  F    R  P  Q  R    S  C  H 1180       1190       1200       1210       1220       1230       1240       1250       1260
CACAGCTTTG AAAACAATCA AAAGAGAGTT TGGCGGCGCA AGATGGTTTG TGGAGGGAGA TATAAAAGGC TGCTTCGATA ATATAGACCA
 T  A  L    K  T  I  K    R  E  F    G  G  A    R  W  F  V    E  G  D    I  K  G    C  F  D  N    I  D  H 1270       1280       1290       1300       1310       1320       1330       1340       1350
CGTTACACTC ATTGGACTCA TCAATCTTAA AATCAAAGAT ATGAAAATGA GCCAATTGAT TTATAAATTT CTAAAAGCAG GTTATCTGGA
 V  T  L    I  G  L  I    N  L  K    I  K  D    M  K  M  S    Q  L  I    Y  K  F    L  K  A  G    Y  L  E 1360       1370       1380       1390       1400       1410       1420       1430       1440
AAACTGGCAG TATCACAAAA CTTACAGCGG AACACCTCAA GGTGGAATTC TATCTCCTCT TTTGGCCAAC ATCTATCTTC ATGAATTGGA
 N  W  Q    Y  H  K  T    Y  S  G    T  P  Q    G  G  I  L    S  P  L    A  N  I    Y  L  H    E  L  D 1450       1460       1470       1480       1490       1500       1510       1520       1530
TAAGTTTGTT TTACAACTCA AAATGAAGTT TGACCGAGAA AGTCCAGAAA GAATAACACC TGAATATCGG GAACTTCACA ATGAGATAAA
 K  F  V    L  Q  L  K    M  K  F    D  R  E    S  P  E  R    I  T  P    E  Y  R    E  L  H  N    E  I  K
```

Fig. 2
(Cont.)

```
           1540       1550       1560       1570       1580       1590       1600       1610       1620
      AAGAATTTCT CACCGTCTCA AGAAGTTGGA GGGTGAAGAA AAAGCTAAAG TTCTTTTAGA ATATCAAGAA AAACGTAAAA GATTACCCAC
       R  I  S   H  R  L     K  L  E    G  E  E     K  A  K  V  L  L  E    Y  Q  E    K  R  K  R   L  P  T 1630       1640       1650       1660       1670       1680       1690       1700       1710
      ACTCCCCTGT ACCTCACAGA CAAATAAAGT ATTGAAATAC GTCCGGTATG CGGACGACTT CATTATCTCT GTTAAAGGAA GCAAAGAGGA
       L  P  C   T  S  Q  T    N  K  V    L  K  Y    V  R  Y  A    D  D  F    I  I  S    V  K  G  S    K  E  D 1720       1730       1740       1750       1760       1770       1780       1790       1800
      CTGTCAATGG ATAAAAGAAC AATTAAAACT TTTTATTCAT AACAAGCTAA AAATGGAATT GAGTGAAGAA AAAACACTCA TCACACATAG
       C  Q  W   I  K  E  Q    L  K  L   F  I  H    N  L  K    M  E  L    S  E  E    K  T  L  I    T  H  S 1810       1820       1830       1840       1850       1860       1870       1880       1890
      CAGTCAACCC GCTCGTTTTC TGGGATATGA TATACGAGTA AGGAGAAGTG GAACGATAAA ACGATCTGGT AAAGTCAAAA AGAAACACT
       S  Q  P   A  R  F  L    G  Y  D    I  R  V    R  R  S  G    T  I  K    R  S  G    K  V  K  K    R  T  L 1900       1910       1920       1930       1940       1950       1960       1970       1980
      CAATGGGAGT GTAGAACTCC TTATTCCTCT TCAAGACAAA ATTCGTCAAT TTATTTTTGA CAAGAAAATA GCTATCCAAA AGAAAGATAG
       N  G  S   V  E  L  L    I  P  L    Q  D  K    I  R  Q  F    I  F  D    K  K  I    A  I  Q  K    K  D  S 1990       2000       2010       2020       2030       2040       2050       2060       2070
      CTCATGGTTT CCAGTTCACA GGAAATATCT TATTCGTTCA ACAGACTTAG AAATCATCAC AATTTATAAT TCTGAATTAA GAGGGATTTG
       S  W  F   P  V  H  R    K  Y  L    I  R  S    T  D  L  E    I  I  T    I  Y  N    S  E  L  R    G  I  C 2080       2090       2100       2110       2120       2130       2140       2150       2160
      TAATTACTAC GGTCTAGCAA GTAATTTTAA CCAGCTCAAT TATTTTGCTT ATCTTATGGA ATACAGCTGT CTAAAAACGA TAGCCTCCAA
       N  Y  Y   G  L  A  S    N  F  N    Q  L  N    Y  F  A  Y    L  M  E    Y  S  C    L  K  T  I    A  S  K 2170       2180       2190       2200       2210       2220       2230       2240       2250
      ACATAAGGGA ACACTTTCAA AAACCATTTC CATGTTTAAA GATGGAAGTG GTTCGTGGGG CATCCCGTAT GAGATAAAGC AAGGTAAGCA
       H  K  G   T  L  S  K    T  I  S    M  F  K    D  G  S  G    S  W  G    I  P  Y    E  I  K  Q    G  K  Q 2260       2270       2280       2290       2300       2310       2320       2330       2340
      GCGCCGTTAT TTTGCAAATT TTAGTGAATG TAAATCCCCT TATCAATTTA CGGATGAGAT AAGTCAAGCT CCTGTATTGT ATGGCTATGC
       R  R  Y   F  A  N  F    S  E  C    K  S  P    Y  Q  F  T    D  E  I    S  Q  A    P  V  L  Y    G  Y  A 2350       2360       2370       2380       2390       2400       2410       2420       2430
      CCGGAATACT CTTGAAAACA GGTTAAAAGC TAAATGTTGT GAATTATGTG GAACATCTGA TGAAAATACT TCCTATGAAA TTCACCATGT
       R  N  T   L  E  N  R    L  K  A    K  C  C    E  L  C  G    T  S  D    E  N  T    S  Y  E  I    H  H  V 2440       2450       2460       2470       2480       2490       2500       2510       2520
      CAATAAGGTC AAAAATCTTA AAGGCAAAGA AAAATGGGAA ATGGCAATGA TAGCGAAACA ACGTAAAACT CTTGTTGTAT GCTTTCATTG
       N  K  V   K  N  L  K    G  K  E    K  W  E    M  A  M  I    A  K  Q    R  K  T    L  V  V  C    F  H  C 2530       2540       2550       2560       2570       2580       2590       2600       2610
      TCATCGTCAC GTGATTCATA AACACAAGTG AATTTTTACG AACGAACAAT AACAGAGCCG TATACTCCGA GAGGGTACG  TACGGTTCCC
       H  R  H   V  I  H  K    H  K  *

2620       2630       2640       2650       2660       2670       2680       2690       2700
      GAAGAGGGTG GTGCAAACCA GTCACAGTAA TGTGAACAAG GCGGTACCTC CCTACTTCAC CATATCATTT TTAATTCTAC GAATCTTTAT 2710       2720       2730       2740       2750       2760       2770
      ACTGGCAAAC AATTTGACTG GAAAGTCATT CCTAAAGAGA AAACAAAAAG CGGCAaagct t
```

Fig. 4
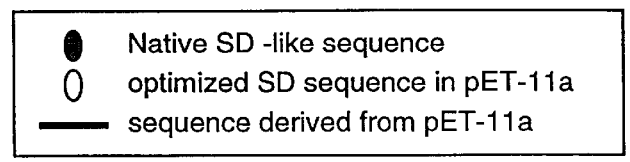
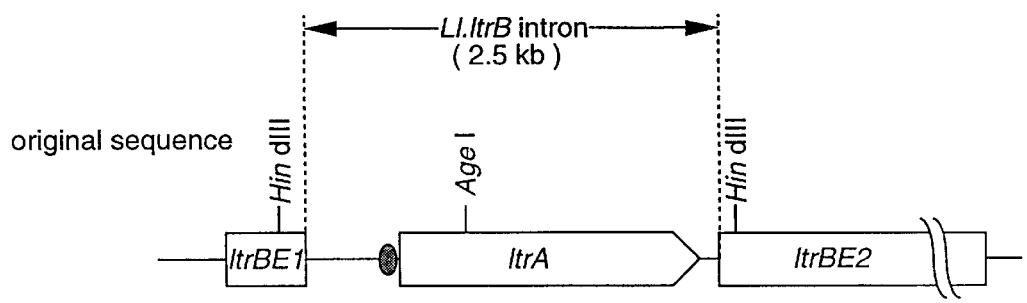
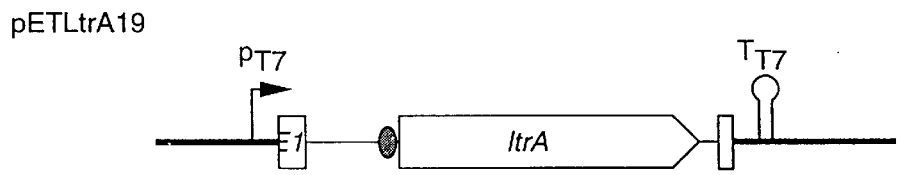
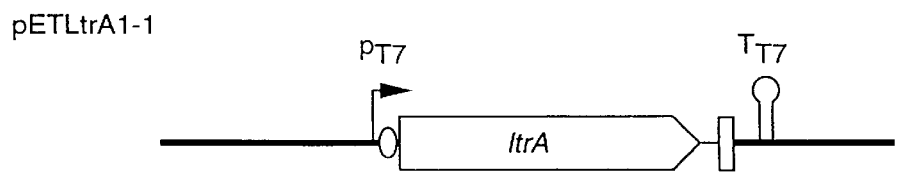

Fig. 5

```
         10         20         30         40         50        | 60
cgctctagaa ctagtggatc cTTGCAACCC ACGTCGATCG TGAACACATC CATAAC ATA 70         80         90        100        110        120
TCATTTTTAA TTCTACGAAT CTTTATACTG Ggaattcgat atcaagctta tcgataccgt 130
cgacctcga
```

METHODS FOR PREPARING NUCLEOTIDE INTEGRASES

BACKGROUND

Nucleotide integrases are molecular complexes that are capable of cleaving double stranded DNA substrates at specific recognition sites and of concomitantly inserting nucleic acid molecules into the DNA substrate at the cleavage site. Thus, nucleotide integrases are useful tools, particularly for genome mapping and for genetic engineering.

Structurally, nucleotide integrases are ribonucleoprotein (RNP) particles that comprise an excised, group II intron RNA and a group II intron-encoded protein, which is bound to the group II intron RNA. At present nucleotide integrases are made by two approaches. The first approach involves isolating the nucleotide integrase from source organisms; both the RNA and protein subunits of the nucleotide integrase are encoded by the DNA in such organisms. In order to obtain nucleotide integrases other than wild type, the source organisms are mutagenized. The mutagenesis is a laborious, multistep process which yields limited quantities of nucleotide integrase.

The second approach used to prepare nucleotide integrases involves combining, in vitro, an exogenous, excised, group II intron RNA, with an RNA-protein complex in which the group II intron-encoded protein is associated with a splicing defective group II intron RNA rather than the excised, group II intron RNA. Therefore, the RNA-protein complex lacks nucleotide integrase activity. The exogenous RNA displaces the splicing defective group II intron RNA to form a nucleotide integrase. The RNA-protein complex is obtained by isolating RNA-protein complex from source organisms. In order to obtain the RNA-protein complex or to obtain a group II intron-encoded protein other than wild type, the source organism must be mutagenized. The mutagenisis is a laborious, multistep process which yields limited quantities of the RNA-protein complex. Thus, this method also provides limited quantities of the nucleotide integrase.

Accordingly, it is desirable to have methods for preparing nucleotide integrase which are not laborious and which permit the nucleotide integrase to be readily modified from the wild type and which do not yield limited quantities of the nucleotide integrase.

SUMMARY OF THE INVENTION

The present invention provides new, improved, and easily manipulable methods for making nucleotide integrases.

In one embodiment, the nucleotide integrase is prepared by introducing a DNA molecule which comprises a group II intron DNA sequence into a host cell. The group II intron DNA sequence is then expressed in the host cell such that RNP particles having nucleotide integrase activity are formed in the cell. Such RNP particles comprise an excise introduced DNA molecule and a group II intron-encoded protein encoded by the introduced DNA molecule. Thereafter, the nucleotide integrase is isolated from the cell.

In another embodiment, the nucleotide integrase is prepared by combining in vitro an excised, group II intron RNA, referred to hereinafter as "exogenous RNA", with a group II intron-encoded protein. Preferably, the exogenous RNA is prepared by in vitro transcription of a DNA molecule which comprises the group II intron sequence. Preferably, the group II intron-encoded protein is made by introducing into a host cell a DNA molecule which comprises the open reading frame sequence of a group II intron, and then expressing the open reading frame sequence in the host cell such that the group II intron-encoded protein encoded by the open reading frame sequence is formed in the cell. Thereafter, the cell is fractionated and the protein is recovered.

In another embodiment, the nucleotide integrase is prepared by combining in vitro an excised, group II intron RNA, referred to hereinafter as "exogenous RNA", with an RNA-protein complex which comprises a group II intron-encoded protein. Preferably, the exogenous RNA is prepared by in vitro transcription of a DNA molecule which comprises the group II intron sequence. Preferably, the RNA-protein complex is made by introducing into a host cell a DNA molecule comprising a group II intron DNA sequence which encodes a splicing-defective group II intron RNA. Thereafter, the cell is fractionated and the RNA-protein complex is isolated.

The present invention also relates to a nucleotide integrase and an improved method for making RNA-protein complexes for use in preparing nucleotide integrases in vitro.

BRIEF DESCRIPTION OF THE DRAWINGS

FIG. 2 shows the nucleotide sequence of the 2.8 kb HindIII fragment that is present in pETLtrA19 and that includes the Ll.HrB intron DNA sequence and portions of the nucleotide sequence of the flanking exons ltrBE1 and ltrBE2, SEQ. ID. NO. 1., the nucleotide sequence of the ltrA open reading frame, SEQ. ID. NO. 2, and the amino acid sequence of the ltrA protein, SEQ. ID. NO. 3.

FIG. 4 is a schematic representation of the inserts in pLE12, pETLtrA19 and pETLtrA1-1.

FIG. 5 is the sequence of the sense strand of the double-stranded DNA substrate, SEQ. ID. NO. 4, which was used to assess the nucleotide integrase activity of the nucleotide integrase which comprise an excised, Ll.ltrB intron RNA and an ltra protein.

DETAILED DESCRIPTION OF THE INVENTION

Nucleotide Integrases

Figure 1:
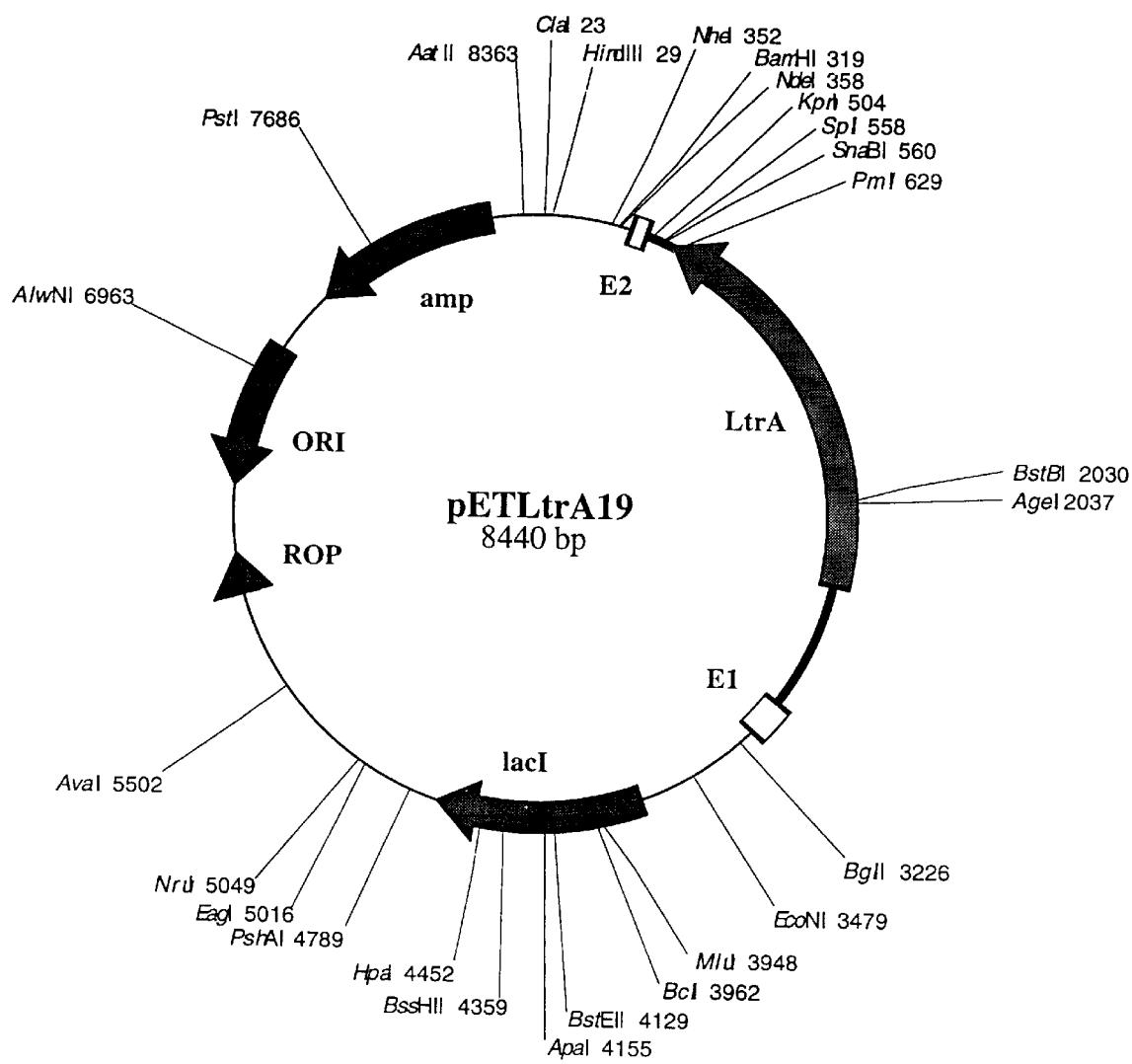
FIG. 1 is the plasmid map of plasmid pETLtrA19.

Nucleotide integrases are enzymes that are capable of cleaving double stranded DNA substrates at specific recognition sites and of concomitantly inserting nucleic acid molecules into the DNA substrate at the cleavage site. The nucleotide integrases insert an RNA molecule into the sense strand of the cleaved DNA substrate and a cDNA molecule into the antisense strand of the cleaved DNA substrate.

Nucleotide integrases are ribonucleoprotein (RNP) particles that comprise an excised group II intron RNA and a group II intron-encoded protein, which is bound to the group II intron RNA. "Excised group II intron RNA," as used herein, refers to the RNA that is, or that is derived from, an in vitro or in vivo transcript of the group II intron DNA and that lacks flanking exon sequences. The excised, group II intron RNA typically has six domains and a characteristic secondary and tertiary structure, which is shown in Saldahana et al., 1993, Federation of the American Society of Experimental Biology Journal, p15–24, which is specifically incorporated herein by reference. The excised, group II intron RNA also includes at least one hybridizing region which is complementary to a recognition site on the substrate DNA. The hybridizing region has a nucleotide sequence, referred to hereinafter as the "EBS sequence", which is complementary to the sequence of the recognition site of the intended substrate DNA, referred to hereinafter as the "IBS sequence". The group II intron-encoded protein has an X domain, a reverse transcriptase domain, and, preferably, a Zn domain. The X domain of the protein has a maturase activity. The Zn domain of the protein has $Zn^{2+}$ finger-like motifs.

Group II intron RNA may be produced containing desired EBS sequences which hybridize to corresponding nucleotides on substrate DNA. In addition, group II intron RNA may be produced containing additional nucleotides in domain IV. In the methods of the present invention both of these group II RNA molecules are produced from an isolated DNA which is then introduced into a cell. Such isolated DNA typically is synthesized using a DNA synthesizer or is genetically-engineered, such as by in vitro site directed mutagenesis.

A. Preparation of the Nucleotide Integrase by Isolation from a Genetically-Engineered Cell.

In one embodiment, the nucleotide integrase is made by introducing an isolated DNA molecule which comprises a group II intron DNA sequence into a host cell. Suitable DNA molecules include, for example, viral vectors, plasmids, and linear DNA molecules. Following introduction of the DNA molecule into the host cell, the group II intron DNA sequence is expressed in the host cell such that excised RNA molecules encoded by the introduced group II intron DNA sequence and protein molecules encoded by introduced group II intron DNA sequence are formed in the cell. The excised group II intron RNA and group II intron-encoded protein are combined within the host cell to produce the nucleotide integrase.

Preferably the introduced DNA molecule also comprises a promoter, more preferably an inducible promoter, operably linked to the group II intron DNA sequence. Preferably, the DNA molecule further comprises a sequence which encodes a tag to facilitate isolation of the nucleotide integrase such as, for example, an affinity tag and/or an epitope tag. Preferably, the tag sequences are at the 5' or 3' end of the open reading frame sequence. Suitable tag sequences include, for example, sequences which encode a series of histidine residues, the Herpes simplex glycoprotein D, i.e., the HSV antigen, or glutathione S-transferase. Typically, the DNA molecule also comprises nucleotide sequences that encode a replication origin and a selectable marker. Optionally, the DNA molecule comprises sequences that encode molecules that modulate expression, such as for example T7 lysozyme.

The DNA molecule comprising the group II intron sequence is introduced into the host cell by conventional methods, such as, by cloning the DNA molecule into a vector and by introducing the vector into the host cell by conventional methods, such as electroporation or by $CaCl_2$-mediated transformation procedures. The method used to introduce the DNA molecule is related to the particular host cell used. Suitable host cells are those which are capable of expressing the group II intron DNA sequence. Suitable host cells include, for example, heterologous or homologous bacterial cells, yeast cells, mammalian cells, and plant cells. In those instances where the host cell genome and the group II intron DNA sequence use different genetic codes, it is preferred that the group II intron DNA sequence be modified to comprise codons that correspond to the genetic code of the host cell. The group II intron DNA sequence, typically, is modified by using a DNA synthesizer or by in vitro site directed mutagenesis to prepare a group II intron DNA sequence with different codons. Alternatively, to resolve the differences in the genetic code of the intron and the host cell, DNA sequences that encode the tRNA molecules which correspond to the genetic code of the group II intron are introduced into the host cell. Optionally, DNA molecules which comprise sequences that encode factors that assist in RNA or protein folding, or that inhibit RNA or protein degradation are also introduced into the cell.

The DNA sequences of the introduced DNA molecules are then expressed in the host cell to provide a transformed host cell. As used herein the term "transformed cell" means a host cell that has been genetically engineered to contain additional DNA, and is not limited to cells which are cancerous. Then the RNP particles having nucleotide integrase activity are isolated from the transformed host cells.

Preferably, the nucleotide integrase is isolated by lysing the transformed cells, such as by mechanically and/or enzymatically disrupting the cell membranes of the transformed cell. Then the cell lysate is fractionated into an insoluble fraction and soluble fraction. Preferably, an RNP particle preparation is isolated from the soluble fraction. RNP particle preparations include the RNP particles having nucleotide integrase activity as well as ribosomes, mRNA and tRNA molecules. Suitable methods for isolating RNP particle preparations include, for example, centrifugation of the soluble fraction through a sucrose cushion. The RNP particles, preferably, are further purified from the RNP particle preparation or from the soluble fraction by, for example, separation on a sucrose gradient, or a gel filtration column, or by other types of chromatography. For example, in those instances where the protein component of the desired RNP particle has been engineered to include a tag such as a series of histidine residues, the RNP particle may be further purified from the RNP particle preparation by affinity chromatography on a matrix which recognizes and binds to the tag. For example, NiNTA Superflow from Qiagen, Chatsworth Calif., is suitable for isolating RNP particles in which the group II intron-encoded protein has a $His_6$ tag.

B. Preparation of the Nucleotide Integrase by Combining Exogenous RNA with a Group II Intron-Encoded Protein to Form a Reconstituted RNP Particle In another embodiment, the nucleotide integrase is formed by combining an isolated exogenous RNA with an isolated group II intron-encoded protein in vitro to provide a reconstituted RNP particle. Preferably the exogenous RNA is made by in vitro transcription of the group II intron DNA. Alternatively, the exogenous RNA is made by in vitro transcription of the group II intron DNA and the DNA of all, or portions, of the flanking exons to produce an unprocessed transcript which contains the group II intron RNA and the RNA encoded by the flanking exons or portions thereof. Then the exogenous RNA is spliced from the unprocessed transcript.

The purified group II intron-encoded protein is prepared by introducing into a host cell an isolated DNA molecule. The introduced DNA molecule comprises the DNA sequence of the open reading frame (ORF) sequence of the group II intron operably linked to a promoter, preferably an inducible promoter. Alternatively, the introduced DNA molecule comprises (1) the ORF sequence and (2) at least some portion of the DNA sequence of the group II intron which lies outside of the ORF sequence and (3) a promoter which is oriented in the DNA molecule to control expression of the ORF sequence. Preferably, the introduced DNA molecule also comprises a sequence at the 5' or 3' end of the group II intron ORF which, when expressed in the host cell, provides an affinity tag or epitope on the N-terminus or C-terminus of the group II intron-encoded protein. Tagging the protein in this manner facilitates isolation of the expressed protein. Thus, the DNA molecule may comprise at the 5' or 3' end of the ORF, for example, a sequence which encode a series of histidine residues, or the HSV antigen, or glutathione-S-transferase. These DNA molecules may also comprise at the 5' or 3' end of the ORF a sequence that encodes thioredoxin or any other molecule which enhances distribution of the protein encoded by the ORF into the soluble fraction of the host cell. Typically, the DNA molecule also comprises nucleotide sequences that encode a replication origin and a selectable marker.

Conventional methods are used to introduce these DNA molecules into any host cell which is capable of expressing the group II intron ORF sequence. For example, the $CaCl_2$-mediated transformation procedure as described by Sambrook et al. in "Molecular Coning A Laboratory Manual", pages 1–82, 1989, can be used to introduce the DNA molecules into *E. coli* cells. Suitable host cells include, for example, heterologous or homologous bacterial cells, yeast cells, mammalian cells, and plant cells. In those instances where the host cells either lack or have limiting amounts of the tRNA molecules for one or more of the codons which are present in the ORF, it is preferred that a DNA molecule encoding the rare tRNA molecules also be introduced into the host cell to increase the yield of the protein. Alternatively, the DNA sequence of the ORF is modified to match the preferred codon usage of the host cell.

The ORP sequence is then expressed in the host, preferably by adding a molecule which induces expression, to provide a transformed host cell. Then the transformed cell is lysed, and preferably fractionated into a soluble fraction and an insoluble fraction. Then the group II intron-encoded protein is isolated, preferably, from the soluble fraction. Methods of isolating the protein from the soluble fraction include, for example, chromatographic methods such as gel filtration chromatography, ion exchange chromatography, and affinity chromatography, which is particularly useful for isolating tagged protein molecules.

Following purification of the group II intron-encoded protein, the protein is incubated with the exogenous RNA, preferably in a buffer, to allow formation of the nucleotide integrase. Optionally, the protein and RNA are denatured prior to the incubation using guanidinium hydrochloride or urea. Then, during incubation, the denaturant is removed in the presence of cosolvents like salts and metal ions to allow proper folding of the protein and RNA in the nucleotide integrase.

C. Preparation of the Nucleotide Integrase by Combining Exogenous RNA With an RNA-Protein Complex.

Alternatively, the nucleotide integrase is prepared by combining the exogenous RNA with an RNA-protein complex that has been isolated from an organism that has been genetically engineered to produce an RNA-protein complex in which the desired group II intron-encoded protein molecules are associated with RNA molecules that include a splicing defective, group II intron RNA but which lack the excised group II RNA. Preferably, the exogenous RNA is prepared by in vitro transcription of a DNA molecule which comprises the group II intron sequence.

Preferably, the RNA-protein complex is made by introducing into a host cell an isolated DNA molecule which comprises a group II intron sequence operably linked to a promoter, preferably an inducible promoter. The group II intron sequence encodes a splicing defective group II intron RNA. Typically, the DNA molecule also comprises nucleotide sequences that encode a replication origin and a selectable marker. Then the group II intron DNA sequence is expressed in the host cell. The group II intron encodes functional group II intron-encoded protein and a splicing-defective group II intron RNA. Thus, the RNA-protein complex made in this manner lack excised, group II RNA molecules that encode the group II intron-encoded protein. The RNA-protein complexes do, however, contain the functional group II intron-encoded protein associated with RNA molecules that comprise the mutant, unspliced form of the group II intron RNA as well as other RNA molecules.

The resulting RNA-protein complex is isolated from the host cell and then incubated with the exogenous RNA, preferably in a buffer, to form the nucleotide integrase. During the incubation the group II intron-encoded protein becomes disassociated from the RNA molecules which are present in the RNA-protein complex and combines with the exogenous RNA to form the nucleotide integrase.

These methods enable production of increased quantities of nucleotide integrases. Conventional methods produce approximately 0.1 to 1 $\mu$g of nucleotide integrase per liter of cultured cells. In the present invention, at least 3 to 10 mg of nucleotide integrase is produced per liter of cultured cells. These methods also offer the further advantage of permitting the sequences of the RNA component and the protein component of the nucleotide integrase to be readily modified.

The following examples of methods for preparing a group II intron-encoded protein and for preparing nucleotide integrases are included for purposes of illustration and are not intended to limit the scope of the invention.

Preparing Nucleotide Integrases In Vivo

EXAMPLE 1

A nucleotide integrase comprising an excised RNA which is encoded by the Ll.ltrB intron of a lactococcal cojugative element prS01 of *Lactococcus lactis* and the protein encoded by the ORF of the Ll.ltrB intron were prepared by transforming cells of the BLR(DE3) strain of the bacterium *Escherichia coli*, which has the recA genotype, with the plasmid pETLtrA19 . Plasmid pETLtrA19, which is schematically depicted in FIG. 1, comprises the DNA sequence for the group II intron Ll.ltrB from *Lactococcus lactis*, shown as a thick line, positioned between portions of the flanking exons ltrBE1 and ltrBE2, shown as open boxes. pETLtrA19 also comprises the DNA sequence for the T7 RNA polymerase promoter and the T7 transcription terminator. The sequences are oriented in the plasmid in such a manner that the ORF sequence, SEQ. ID. NO. 2, within the Ll.ltrB intron is under the control of the T7 RNA polymerase promoter. The ORF of the Ll.ltrB intron, shown as an arrow box, encodes the protein ltra. The sequence of the Ll.ltrB intron and the flanking exon sequences present in pETLtrA19 are shown in FIG. 2 and SEQ.ID. NO. 1. Vertical lines in FIG. 2 denote the junctions between the intron and the flanking sequences. The amino acid sequence of the ltra protein, SEQ. ID. NO. 3 is shown under the ORF sequence, SEQ. ID. NO. 2, in FIG. 2. The exon binding sites are encoded by sequences from and including nucleotides 457 go and including 463 (EBS1) from and including nucleotides 401 to and including nucleotides 406 (EBS2a), and from and including nucleotides 367 to and including 367–372 (EBS2b). Domain IV is encoded by nucleotide 705 to 2572.

pETLtrA19 was prepared first by digesting pLE12, which was obtained from Dr. Gary Dunny from the University of Minnesota, with HindIII and isolating the restriction fragments on a 1% agarose gel. A 2.8 kb HindIII fragment which contains the Ll.ltrB intron together with portions of the flanking exons ltrBE1 and ltrBE2 was recovered from the agarose gel and the single-stranded overhangs were filled in with the Klenow fragment of DNA polymerase I obtained from Gibco BRL, Gaithersburg, Md. The resulting fragment was ligated into plasmid pET-11a that had been digested with XbaI and treated with Klenow fragment. pET-11 a was obtained from Novagen, Madison, Wis.

pETLtrA19 was introduced into the $E.$ $coli$ cells using the conventional $CaCl_2$-mediated transformation procedure of Sambrook et al. as described in "Molecular Coning A Laboratory Manual", pages 1–82, 1989. Single transformed colonies were selected on plates containing Luria-Bertani (LB) medium supplemented with ampicillin to select the plasmid and with tetracycline to select the BLR strain. One or more colonies were inoculated into 2 ml of LB medium supplemented with ampicillin and grown overnight at 37° C. with shaking. 1 ml of this culture was inoculated into 100 ml LB medium supplemented with ampicillin and grown at 37° C. with shaking at 200 rpm until $OD_{595}$ of the culture reached 0.4. Then isopropyl-beta-D-thiogalactoside was added to the culture to a final concentration of 1 mM and incubation was continued for 3 hours. Then the entire culture was harvested by centrifugation at 2,200×g, 4° C., for 5 minutes. The bacterial pellet was washed with 150 mM NaCl and finally resuspended in 1/20 volume of the original culture in 50 mM Tris, pH 7.5, 1 mM EDTA, 1 mM DTT, and 10% (v/v) glycerol (Buffer A). Bacteria were frozen at −70° C.

To produce a lysate the bacteria were thawed and frozen at −70° C. three times. Then 4 volumes of 500 mM KCl, 50 mMCaCl2, 25 mM Tris, pH 7.5, and 5 mM DTT (HKCTD) were added to the lysate and the mixture was sonicated until no longer viscous, i.e for 5 seconds or longer. The lysate was fractionated into a soluble fraction and insoluble fraction by centrifugation at 14,000×g, 4° C., for 15 minutes. Then 5 ml of the resulting supernatant, i.e., the soluble fraction, were loaded onto a sucrose cushion of 1.85M sucrose in HKCTD and centrifuged for 17 hours at 4° C., 50,0000 rpm in a Ti 50 rotor from Beckman. The pellet which contains the RNP particles was washed with 1 ml water and then dissolved in 25 μl 10 mM Tris, pH 8.0, 1 mM DTT on ice. Insoluble material was removed by centrifugation at 1,500×g, 4° C., for 5 minutes. The yield of RNP particles prepared according to this method comprise the excised Ll.ltrB intron RNA and the ltra protein.

EXAMPLE 2

A nucleotide integrase comprising the ltra protein and the excised Ll.ltrB intron RNA was prepared as described in example 1 except the plasmid pETLtrA19 was used to transform cells of the BL21(D3) strain of $E.$ $coli.$

EXAMPLE 3

A nucleotide integrase was prepared by transforming cells of the $E.$ $coli$ strains BLR(DE3) with pETLtrA19 as described in Example 1 except that the transformed $E.$ $Coli$ were grown in Super-Broth (SOB) medium and shaken at 300 rpm during the 3 hour incubation.

EXAMPLE 4

A nucleotide integrase was prepared by transforming cells of the $E.$ $coli$ strain BL21(DE3) with pETLtrA19 as described above in Example 2 except the cells were also transformed with plasmid pOM62 which is based on the plasmid pACYC184 and has an approximately 150 bp insert of the argU(dnaY) gene at the EcoRI site. The argU gene encodes the tRNA for the rare arginine codons AGA and AGG. The ltrA gene contains 17 of the rare arginine codons. The transformed cells were grown in SOB medium as described in Example 3 and fractionated into a soluble fraction and an insoluble fraction as described in Example 1.

Preparing a Group II Intron-Encoded Protein Having a Purification Tag on the C Terminus

EXAMPLE 5

To facilitate purification of the protein, the ltrA ORF was tagged at the C-terminus with a $His_6$ affinity tag and an epitope derived from the Herpes simplex virus glycoprotein D. The plasmid adding the tags was made in two steps by using PCR. In the first step, a fragment containing exon 1 and the ltrA ORF was amplified using primers LtrAex1.Xba having the sequence 5' TCACCTCATCTAGA-CATTTTCTCC 3', SEQ. ID. NO. 5 which introduces an Xba I site in exon 1 of ltrB, and ltrA expr3 5'CGTTCG-TAAAGCTAGCCTTGTGTTTATG 3', SEQ. ID. NO. 6, which substitutes a CGA (arginine) codon for the stop codon and introduces an Nhe I site at the 3' end of the LtrA ORF. The PCR product was cut with XbaI and Nhe I, and the restriction fragments gel purified and cloned into pET-27b (+), cut with Xba I and Nhe I obtained from Novagen, Madison, Wis. The resulting plasmid pIntermediate-C fuses the 3' end of the ltrA ORF to an HSV tag and $His_6$ purification tag, both of which are present on the vector pET-27b(+). In a second step, intron sequences 3' to the ORF and exon 2 were amplified using pLE12 as a substrate and the 5' primer LtrAConZn1, having the sequence 5'CACAAGTGATCATTTACGAACG 3', SEQ. ID. No. 7 and the 3' primer LtrAex2, which has the sequence 5'TTGG-GATCCTCATAAGCTTT GCCGC 3', SEQ. ID. NO. 8. The PCR product was cut with Bcl1 and BamH1, the resulting fragment filled in, gel-purified and cloned into pIntermediate-C, which had been cleaved with Bpu11021 and filled in. The resulting plasmid is designated pC-hisLtrA19.

Cells of the BLR(DE3) strain of $E.$ $coli$ were transformed as described in example 1 with pIntermediate-C and cultured at 37° C. for 3 hours in SOB medium as described in example 3. The cells were also fractionated into a soluble fraction, which contains RNP particles, and an insoluble fraction as described in example 1.

EXAMPLE 6

To facilitate purification of the protein, the ltrA ORF was tagged at the N-terminus with a $His_6$ affinity tag and the epitope tag XPRESS™ which was obtained from Invitrogen, San Diego, Calif. The plasmid adding the tags was made in two steps by using PCR. In the first step, a fragment was made in two steps by using PCR mutagenesis. In the first step, the ltrA ORF and 3' exon were amplified and BamH1 sites were appended to both the 5' an 3' end of the ltrA ORF using pLE12 as a substrate and the following pair: 5' primer N-LtrA 5', having the sequence 5'CAAAGGATC-CGATGAAACCAACAATGGCAA 3', SEQ. ID. NO. 9; and the 3' primer LtrAex2, SEQ. ID. NO. 8. The PCR product was cut with BamH1 and the resulting restriction fragment was gel purified and cloned into the BamH1 site of plasmid pRSETB obtained from Invitrogen, San Diego, Calif. The resulting plasmid pIntermediate-N fuses the N-terminus of the ltrA ORF to a $His_6$ purification tag, and adds an XPRESS™ epitope tag from the vector. In a second step, the 5' exon and Ll.ltrB intron sequences 5' to the ORF were amplified using pLE12 as a substrate and the 5' primer NdeLTR5, having the sequence 5'AGTGGCTTCCATAT-GCTTGGTCATCACCTCATC 3', SEQ. ID. No. 10 and 3' primer NdeLTR3', which has the sequence 5' GGTAGAAC-CATATGAAATTCCTCCTCCCTAATCAATTTT 3', SEQ. ID. NO. 11. The PCR product was cut with Nde I, filled in, the fragment gel purified and cloned into pIntermediate-N, which had also been cut with Nde I. Plasmids were screened for the orientation of the insert, and those oriented such that the 5' exon was proximal to the T7 promoter were used to transform the host cells. The resulting plasmid pFinal-N expresses a message under the control of the T7 polymerase promoter which comprises the E1 and E2 portions of the exons ltrBE1 and ltrBE2, and the ltrA ORf fused at the 5' end with an $His_6$ purification tag and the XPRESS™ epitope tag.

Cells of the BLR(DE3) strain of *E. coli* were transformed as described in example 1 with pIntermediate-N and cultured at 37° C. for 3 hours in SOB medium as described in example 3. The cells were also fractionated into a soluble fraction, which contains RNP particles, and an insoluble fraction as described in example 1.

EXAMPLE 7

Figure 3:
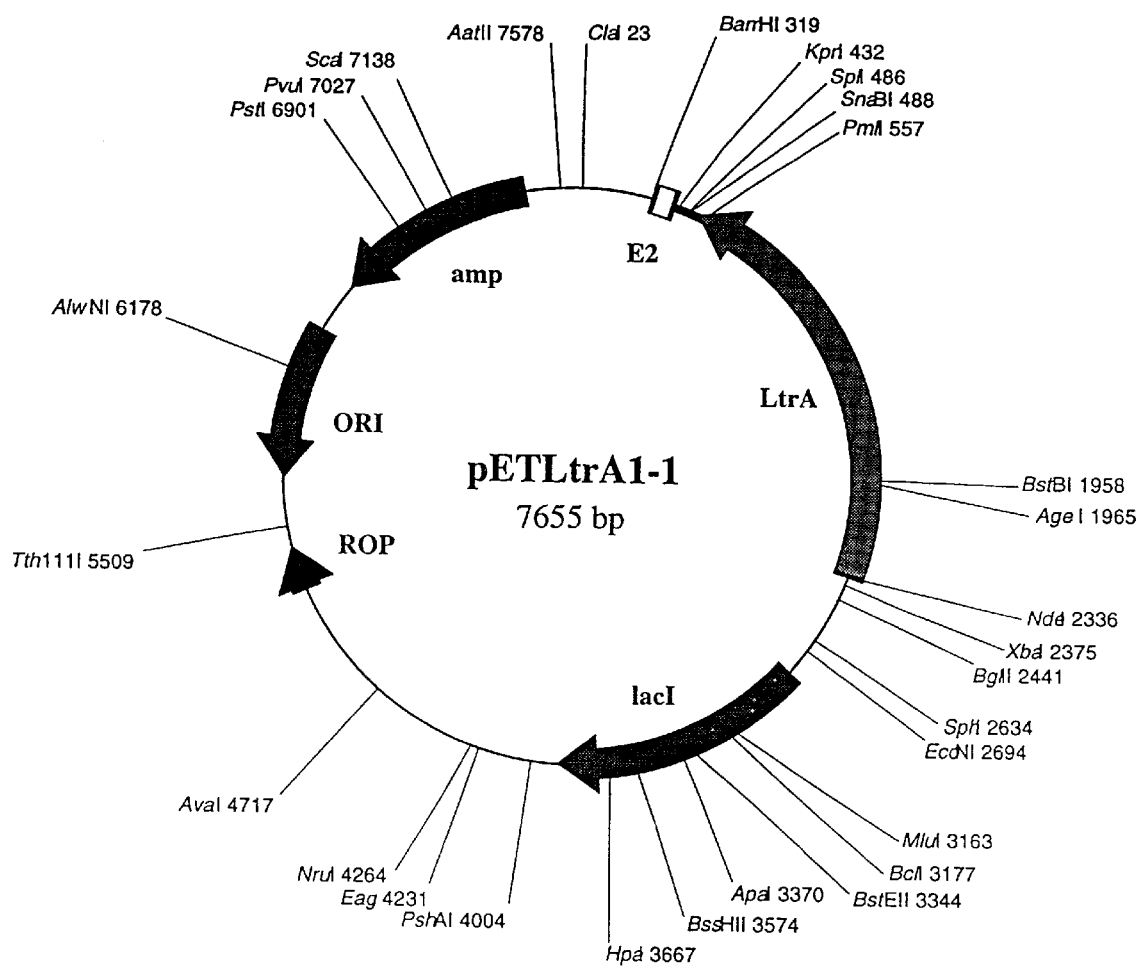
FIG. 3 is the plasmid map of plasmid pETLtrA1-1.

Plasmid pETLtrA1-1 was used to prepare a partially-purified preparation of the ltra protein, which is encoded by the ORF of the Ll.trB intron. Plasmid pETLtrA1-1 is a derivative of pETLtrA19 and lacks exon 1 and the intron sequences upstream of the ltrA ORF. Accordingly, the ltrA ORF is directly downstream of the phage T7 promoter following the Shine-Dalgarno sequence in the plasmid. The plasmid map of pETLtrA1-1 is shown in FIG. 3.

pETLtrA1-1 was made by using the polymerase chain reaction to amplify the ltrA ORF using the 5' primer LtrAexpr 5'AAAACCTCCATATG AAACCAACAATG 3', SEQ. ID. NO. 12, which introduces an NdeI site and 3' primer LtrAex2, SEQ.ID.NO. 8. The PCR product was cut with NdeI and BamHI, gel purified on a 1% agarose gel, and cloned into pET-11a. The inserts of pLE12, pETLtrA19 and pETLtrA1-1, each of which contain the ltrA ORF is depicted in FIG. 4.

pETLtrA1-1 was introduced into cells of the *E. coli* strain BLR(DE3) as described in Example 1 and the transformed cells grown for 3 hours in SOB medium at 37° C. as described in Example 3. Thereafter, the cells were lysed and the resulting lysate fractionated into a soluble fraction and insoluble fraction by low speed centrifugation as described in Example 1.

Preparing a Nucleotide Integrase In Vitro

EXAMPLE 8

A nucleotide integrase is prepared in vitro by combining an exogenous RNA comprising an excised Ll.ltrB intron RNA with a purified LtrA protein. The purified LtrA is obtained by subjecting the partially-purified ltra protein of example 7 to standard chromatographic methods. The exogenous RNA is prepared by cloning the Ll.ltrB intron together with its flanking exons into a plasmid downstream of a T7 promoter, linearizing the plasmid downstream of the exon 2 using a restriction enzyme, and transcribing the intron with T7 RNA polymerase. The in vitro transcript is incubated for one hour at 37° C. in 500 mM $NH_4Cl$ and 50 mM $MgCl_2$, 10 mM DTT, 2 units RNase inhibitor, to increase or produce excised intron RNA. The exogenous RNA and purified ltra protein are then incubated in a buffer to form the nucleotide integrase. The nucleotide integrase is then isolated from the reaction mixture.

COMPARATIVE EXAMPLE A

RNP particles were prepared as described in Example 1 from cells of the BLR(DE3) strain of *E. coli* that had been transformed with plasmid pET11a, which lacks a group II intron. Accordingly, these RNP particles do not comprise excised, group II RNA or group II intron-encoded proteins and therefore, do not have nucleotide integrase activity.

COMPARATIVE EXAMPLE B

RNP particles were prepared as described in Example 1 from cells of the BLR(DE3) strain of *E. coli* that had been transformed with plasmid pETLtrA19FS, which comprises the sequence of an ltrA ORF having a frame shift 372 base pairs downstream from the initiation codon of the ltrA ORF. frame. Accordingly, these RNP particles contain a truncated ltra protein, i.e. an ltra protein lacking the Zn domain and, therefore, do not have nucleotide integrase activity.

Characterization of the RNP Particles of Examples 1 and 2

A portion of the RNP particle preparation of examples 1 and 2 and comparative examples A and B were subjected to SDS gel electrophoresis. Staining of the resulting gel with Coomasie Blue permitted visualization of the proteins in each of the fractions. A band of approximately 70 kDa, which corresponds to the predicted molecular weight of the ltra protein was seen in the lanes containing aliquots of the RNP particles of Examples 1 and 2. This band was absent from the lanes containing the RNP particles prepared from comparative examples A and B. On the basis of the staining intensity of the 70 kDa band, the quantity of ltra protein in 10 $OD_{260}$ units of RNP particles was estimated to be approximately 3 µg. These results indicate that RNP particles containing the group II intron-encoded protein ltra can be prepared by expression of the group II intron Ll.ltrB in a heterologous host cell.

The reverse transcriptase activities of the RNP particles of examples 1 and 2 and the RNP particles of comparative examples A and B were assayed by incubating each of the RNP particle preparations with a poly(rA) template and oligo (dT18) as a primer. The RNP particles of examples 1 and 2 exhibited reverse transcriptase activity, while the RNP particles of comparative examples A and B exhibited no reverse transcriptase activity. These results indicate that the methods described in examples 1 and 2 are useful for preparing RNP particles that have reverse transcriptase activity. The reverse transcriptase activity that is present in nucleotide integrases allows incorporation of a cDNA molecule into the cleavage site of the double stranded DNA which is cut by the nucleotide integrase.

Characterizing the Distribution and Yield of the ltra Protein

A portion of the insoluble fraction and soluble fraction of the lysates from the cells transformed and cultured according to the methods described in examples 1, 2, 3, and 4 were subjected to SDS polyacrylamide gel electrophoresis. Following electrophoresis, the SDS gels were stained with Coomassie blue to compare the yield of the ltra protein and the distribution of the 70 kDa ltra protein prepared by the methods of examples 1, 2, 3, and 4. The results of this assay demonstrated that more of the ltra protein was found in the soluble fraction when the transformed BLR (DE3) cells were grown in SOB medium and shaken at 300 rpm than when the transformed BLR cells were grown in LB medium and shaken at 200 rpm, These results also indicated that the total amount of ltra protein produced by the transformed BLR cells, that is the amount of LtrA in both the soluble and insoluble fractions, increased when a plasmid comprising the Ll.ltrB intron and a plasmid comprising argU(dnaY) gene were both introduced into the host cells.

Characterization of the Group II Intron-Encoded Protein Prepared According to the Methods of Examples 5 and 6

A portion of the insoluble fraction and soluble fractions of the lysates from the cells transformed and cultured according to the methods described in examples 5 and 6 and in comparative examples A and B were subjected to electrophoresis on duplicate SDS-polyacrylamide gels. One of the gels was stained with Coomasie blue and the proteins on the duplicate were transferred to nitrocellulose paper by Western blotting. A primary antibody to the HSV antigen or the and an alkaline phosphatase-labeled anti-mouse IgG secondary antibody were used in an enzyme-linked immunoassay to identify proteins carrying the HSV epitope or the XPRESS™. The results of these assays showed that the anti-HSV antibody and the anti-XPRESS™ antibody bound to a protein having a molecular weight of approximately 70 kDa, which is the molecular weight of the ltra protein. The HSV tagged ltra protein and the xpress™ tagged ltra protein were found in the soluble and insoluble fractions from cells transformed with pIntermediateC and bIntermediateN but not in the soluble fractions and insoluble fractions of cells transformed with pet 27b(+) and pRSETB. Thus, the methods of examples 5 and 6 are useful for preparing a tagged group II intron encoded protein. These assays also demonstrated that the amount of the tagged group II intron-encoded protein present in the soluble fraction, from which the RNP particles are derived, increases when the transformed and induced cells are incubated at 28° C. as compared to 37° C. Alternative studies showed that incubation times of 30 minutes to 3 hours resulted in production of the tagged protein, but these incubation times resulted in production of less of the protein and are therefore less preferred.

Using the RNP Particles to Cleave Double-Stranded DNA and to Insert Nucleotide Sequences into the Cleavage Site.

Nucleotide integrases are useful for cleaving one or both strands of a double-stranded DNA substrate, catalyzing the attachment of the excised, group II intron RNA molecule to one of the strands of the substrate DNA and catalyzing the formation of a cDNA molecule on the other strand of the cleaved double-stranded DNA substrate. Thus, the nucleotide integrases are useful analytical tools for determining the location of a defined sequence in a double-stranded DNA substrate. Moreover, the simultaneous insertion of the nucleic acid molecule into the first strand of DNA permits tagging of the cleavage site of the first strand with a radiolabeled molecule. In addition, the automatic attachment of an RNA molecule onto one strand of the DNA substrate permits identification of the cleavage site through hybridization studies that use a probe that is complementary to the attached RNA molecule. An attached RNA molecule that is tagged with a molecule such as biotin also enables the cleaved DNA to be affinity purified. Moreover, the cleavage of one or both strands of the double stranded DNA and the concomitant insertion of a nucleotide sequence into the cleavage site permits incorporation of new genetic information or a genetic marker into the cleavage site, as well as disruption of the cleaved gene. Thus, the nucleotide integrases are also useful for rendering the substrate DNA nonfunctional or for changing the characteristics of the RNA and protein encoded by the substrate DNA.

While nucleotide integrases can be used to cleave double-stranded DNA substrates at a wide range of temperatures, good results are obtained at a reaction temperature of from about 30° C. to about 42° C., preferably from about 30° to about 37° C. A suitable reaction medium contains a monovalent cation such as $Na^+$ or $K^+$, and a divalent cation, preferably a magnesium or manganese ion, more preferably a magnesium ion, at a concentration that is less than 100 mM and greater than 1 mM. Preferably the divalent cation is at a concentration of about 5 to about 20 mM. The preferred pH for the medium is from about 6.0–8.5, more preferably about 7.5–8.0.

Cleavage of 3' and 5' End Labeled Double Stranded DNA 0.025 $O.D._{260}$ of the RNP particles of Example 1 and comparative examples A and B were incubated for 20 minutes with 150,000 cpm of each of a 5' and 3' end-labeled DNA substrate that comprises the exon 1 and exon 2 junction of the ltrB gene. The sequence of the 129 base pair substrate, which comprises the 70 base pair exon 1 and exon 2 junction of the ltrB gene, plus sequences of the plasmid is depicted in FIG. 5 and SEQ. ID. NO. 4. To verify cleavage, the products were isolated on a 6% polyacrylamide gel.

Figure 6:
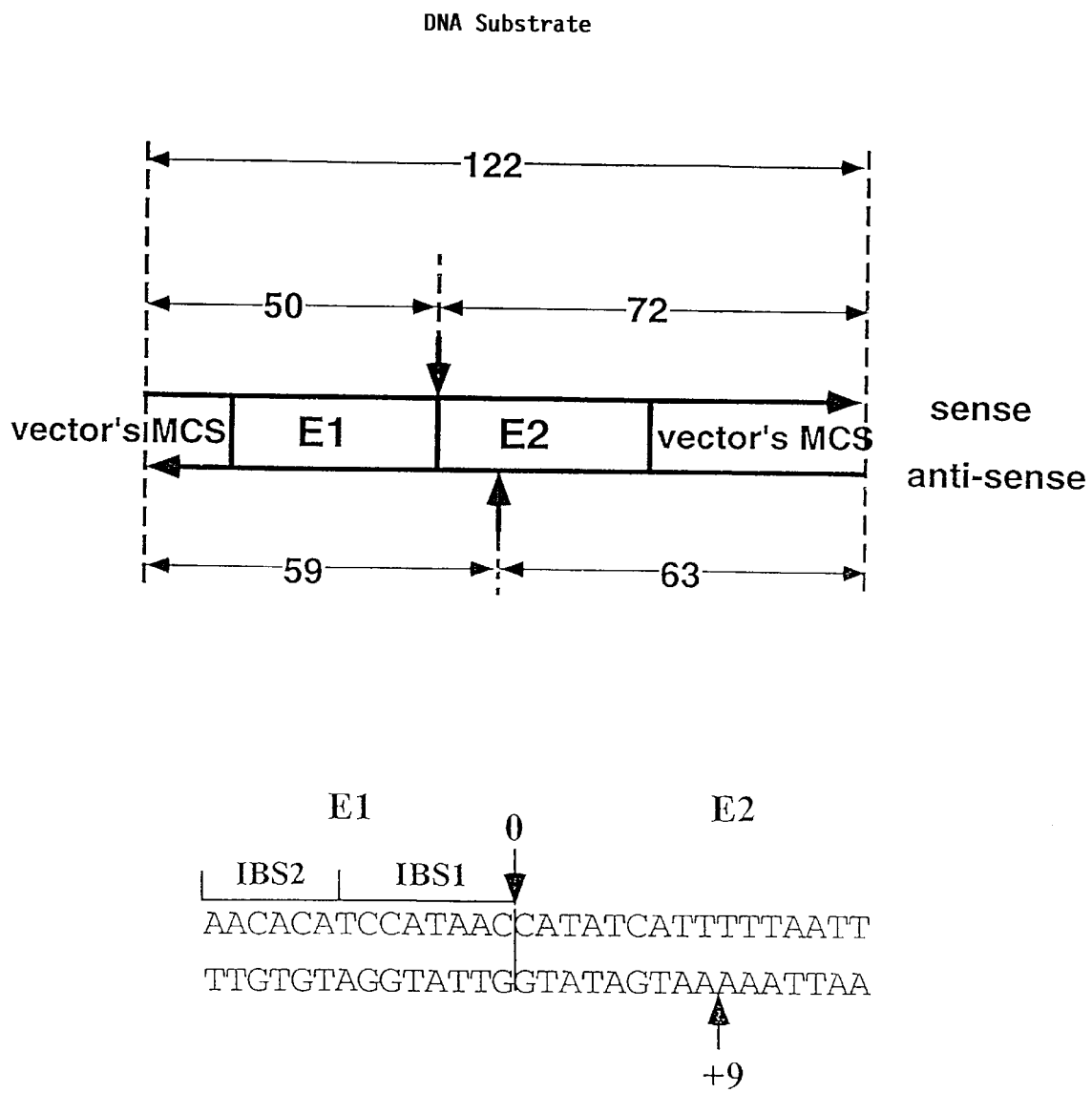
FIG. 6a is a schematic depiction of the substrate which is cleaved by the nucleotide integrase comprising Ll.ltrB intron RNA and the ltra protein.
FIG. 6b shows the IBS1 and IBS2 sequences of the substrate and the cleavage sites of the double-stranded DNA substrate which is cleaved by this integrase.

The substrate which is cleaved by the nucleotide integrase comprisesing the excised Ll.trB intron RNA and the ltra protein is schematically depicted in FIG. 6(a). In addition, the IBS1 and IBS2 sequence of the substrate is shown in FIG. 6(b). As shown in FIG. 6, the IBS1 and IBS2 sequences which are complementary to the EBS sequences of the Lltr.B intron RNA are present in exon 1 of the ltrB gene. As depicted in FIG. 6, the RNP particles prepared according to the method of example 1 cleaved the sense strand of the substrate at position 0, which is the exon 1 and exon 2 junction, and the antisense strand at +9. When the RNP particles of prepared according to the method of example 1 were treated with either RNase A/T1 to degrade the RNA in the particles, or with proteinase K to degrade the protein component of the particles prior to incubation of the particles with the substrate, no cleavage of the substrate was observed. These results indicate that both the RNA component and the protein component of the nucleotide integrase are needed to cleave both strands of the substrate DNA.

Cleaving Both Strands of Double-Stranded DNA and Inserting the Intron RNA of the Nucleotide Integrase into the Cleavage Site 0.025 $O.D._{260}$ units of the RNP particle preparation of example 1 were reacted with 125 fmoles (150,000 cpm) of the 129 base pair internally-labeled DNA substrate for 20 minutes. To verify cleavage, the products were glyoxalated and analyzed in a 1% agarose gel.

A dark band of radiolabel of approximately 1.0 kb RNA and a lighter bands of approximately 0.8, 1.1, 1.4, 1.5, 1.6, 1.9, 2.5, 3.2 were observed on the gel. Pretreatment of the reaction products with RNase prior to isolation on the agarose gel resulted in the complete disappearance of these bands. These results indicate that Ll.trB intron RNA was attached to the DNA substrate during reaction of the substrate with the RNP particles of example 1. On the basis of the size of Ll.trB intron, it is believed that the band at 2.5 kb represents the integration of the full length group II intron RNA into the cleavage site of the sense strand. The presence of smaller radiolabeled products on the gel is believed to be due to degradation of the integrated intron RNA by RNases which may be present in the RNP particle preparation. The finding that the RNA-DNA products withstand denaturation with glyoxal indicates a covalent linkage between the intron RNA and the DNA substrate.

What is claimed is:

1. A method for preparing a nucleotide integrase which cleaves a double-stranded DNA substrate, said method comprising the following steps:
(a) providing a DNA molecule comprising a group II intron DNA sequence, wherein the group II intron DNA sequence encodes a group II intron RNA and comprises an open reading frame sequence which encodes a group II intron-encoded protein;
(b) introducing the DNA molecule into a host cell;
(c) expressing the group II intron DNA sequence in the host cell, to provide an excised group II intron RNA and a group II intron-encoded protein molecule, wherein the protein and the RNA combine in the host cell to form the nucleotide integrase;
(d) obtaining the nucleotide integrase of step (c) from the host cell.

2. The method of claim 1 wherein the DNA molecule further comprises a promoter operably linked to the group II intron DNA sequence.

3. The method of claim 2 wherein the promoter is an inducible promoter.

4. The method of claim 2 wherein the DNA molecule further comprises a nucleotide sequence which encodes a tag for facilitating isolation of the nucleotide integrase from the host cell; and wherein the method further comprises expressing the nucleotide sequence which encodes the tag in the host cell to provide a tagged group II intron-encoded protein; and wherein step (d) involves employing the tag to recover the nucleotide integrase.

5. The method of claim 4 wherein the sequence which encodes the tag is located at the 5' end or the 3' end of the open reading frame sequence of the group II intron DNA sequence.

6. The method of claim 2 further comprising the steps of:

introducing a DNA sequence encoding at tRNA which corresponds to the genetic code of the group II intron DNA sequence into the host cell before step (b) and expressing the tRNA-encoding DNA sequence in the host cell.

7. The method of claim 1 wherein the DNA molecule is prepared by the following steps of:

preparing a synthetic group II intron DNA sequence; wherein the group II intron DNA sequence comprises a sequence of nucleotides that bind to the recognition site of the substrate DNA; and incorporating the synthetic group II intron DNA sequence into the DNA molecule.

8. The method of claim 1 wherein the group II intron DNA sequence comprises the DNA sequence of the Ll.ltrB intron and the RNP particles comprise an excised Ll.ltrB intron RNA and an ltra protein.

9. The method of claim 1 wherein the group II intron DNA sequence comprises a modified DNA sequence of the Ll.ltrB intron and the RNP particles comprise a modified excised Ll.ltrB intron RNA and an ltra protein molecule.

10. The method of claim 1 wherein the group II inton DNA sequence comprises a modified DNA sequence of the Ll.ltrB intron and the RNP particles comprise a modified excised Ll.ltrB intron RNA and a modified ltra protein molecule.

11. The method of claim 1 wherein the host cell is *E. coli*.

12. The method of claim 8 wherein the host cell is *E. coli*.

13. A method of preparing a nucleotide integrase in vitro comprising the steps of:

(a) providing an isolated, excised, group II intron RNA;

(b) providing an isolated group II intron-encoded protein; and (c) incubating the excised, group II intron RNA with the group II intron-encoded protein for a sufficient time to form a nucleotide integrase comprising the excised, group II intron RNA bound to the group II intron-encoded protein.

14. The method of claim 13 wherein the group II intron-encoded protein is produced by a process comprising the steps of:

(a) providing a DNA molecule comprising an open reading frame sequence of a group II intron, said open reading frame sequence being operably linked to a promoter;

(b) introducing the DNA molecule of step (a) into a host cell;

(c) expressing the open reading frame sequence in the host cell to provide the group II intron-encoded protein; and (d) isolating the group II intron-encoded protein from the host cell.

15. The method of claim 13 wherein the DNA molecule further comprises a sequence which encodes a tag that facilitates isolation of the group II intron-encoded protein from the host cell; and wherein the method further comprises expressing the nucleotide sequence which encodes the tag in the host cell to provide a tagged group II intron-encoded protein; and wherein step (d) involves obtaining a tagged nucleotide integrase from the host cell.

16. The method of claim 15 wherein the sequence which encodes the tag is located at a position selected from the 5' end and the 3' end of the open reading frame sequence.

17. The method of claim 13 wherein the open reading frame sequence encodes the ltrA protein and wherein the excised, group II RNA is selected from the group consisting of an unmodified, excised Ll.ltrB intron RNA and a modified, excised Ll.ltrB intron RNA.

18. A method of preparing a nucleotide integrase in vitro comprising the steps of:

(a) providing an exogenous RNA which comprises an excised group II intron RNA;

(b) providing an RNA-protein complex, wherein the RNA-protein complex comprises a protein having an amino acid sequence encoded by a group II intron and RNA that is free of excised, group II intron RNA molecules having a sequence that encodes said protein; said RNA-protein complex being prepared by the following steps:

(i) providing an isolated DNA molecule comprising a group II intron DNA sequence, wherein said group II intron DNA sequence encodes a group II intron-encoded protein and a splicing defective group II RNA (ii) introducing the DNA molecule into a host cell;

(iii) expressing the mutated group II intron DNA sequence in the host cell, wherein an RNA-protein complex comprising the group II intron-encoded protein and the splicing-defective group II RNA are formed in the cell (iv) obtaining the RNA-protein complex of step (iii) from the host cell; and (c) incubating the exogenous RNA of step (a) with the RNP particle preparation for a sufficient time to form a nucleotide integrase comprising the excised group II RNA and the protein having an amino acid sequence encoded by a group II intron.

19. An isolated nucleotide integrase comprising an excised Ll.ltrB intron RNA and an ltra protein molecule.

* * * * *

UNITED STATES PATENT AND TRADEMARK OFFICE
CERTIFICATE OF CORRECTION

PATENT NO. : 5,804,418  
APPLICATION NO. : 08/752238  
DATED : September 8, 1998  
INVENTOR(S) : Alan Marc Lambowitz et al.

Page 1 of 1

It is certified that error appears in the above-identified patent and that said Letters Patent is hereby corrected as shown below:

In the Specification

Column 1, Line 3 add Government Support Clause "This invention was made with government support under grant number 2008-55112-18760 awarded by the National Institute of Food and Agriculture. The government has certain rights in the invention."

Signed and Sealed this
Eighth Day of December, 2020

Andrei Iancu
*Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2761 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AAGCTTAGAG   AAAAATAATG   CGGTGCTTGG   TCATCACCTC   ATCCAATCAT   TTTCTCCTGA         60
TGACAATCTA   ACTCCTGAAC   AAATTCATGA   AATAGGTCGT   CAAACCATAT   TAGAATTTAC        120
AGGTGGCGAA   TATGAATTTG   TGATTGCAAC   CCACGTCGAT   CGTGAACACA   TCCATAACGT        180
GCGCCCAGAT   AGGGTGTTAA   GTCAAGTAGT   TTAAGGTACT   ACTCTGTAAG   ATAACACAGA        240
AAACAGCCAA   CCTAACCGAA   AAGCGAAAGC   TGATACGGGA   ACAGAGCACG   GTTGGAAAGC        300
GATGAGTTAC   CTAAAGACAA   TCGGGTACGA   CTGAGTCGCA   ATGTTAATCA   GATATAAGGT        360
ATAAGTTGTG   TTTACTGAAC   GCAAGTTTCT   AATTTCGGTT   ATGTGTCGAT   AGAGGAAAGT        420
GTCTGAAACC   TCTAGTACAA   AGAAAGGTAA   GTTATGGTTG   TGGACTTATC   TGTTATCACC        480
ACATTTGTAC   AATCTGTAGG   AGAACCTATG   GGAACGAAAC   GAAAGCGATG   CCGAGAATCT        540
GAATTTACCA   AGACTTAACA   CTAACTGGGG   ATACCCTAAA   CAAGAATGCC   TAATAGAAAG        600
GAGGAAAAAG   GCTATAGCAC   TAGAGCTTGA   AAATCTTGCA   AGGGTACGGA   GTACTCGTAG        660
TATTCTGAGA   AGGGTAACGC   CCTTTACATG   GCAAGGGGT    ACAGTTATTG   TGTACTAAAA        720
TTAAAAATTG   ATTAGGGAGG   AAAACCTCAA   AATGAAACCA   ACAATGGCAA   TTTTAGAAAG        780
AATCAGTAAA   AATTCACAAG   AAAATATAGA   CGAAGTTTTT   ACAAGACTTT   ATCGTTATCT        840
TTTACGTCCA   GATATTTATT   ACGTGGCGTA   TCAAAATTTA   TATTCCAATA   AAGGAGCTTC        900
CACAAAAGGA   ATATTAGATG   ATACAGCGGA   TGGCTTTAGT   GAAGAAAAAA   TAAAAAGAT         960
TATTCAATCT   TTAAAGACG    GAACTTACTA   TCCTCAACCT   GTACGAAGAA   TGTATATTGC       1020
AAAAAAGAAT   TCTAAAAAGA   TGAGACCTTT   AGGAATTCCA   ACTTTCACAG   ATAAATTGAT       1080
CCAAGAAGCT   GTGAGAATAA   TTCTTGAATC   TATCTATGAA   CCGGTATTCG   AAGATGTGTC       1140
TCACGGTTTT   AGACCTCAAC   GAAGCTGTCA   CACAGCTTTG   AAAACAATCA   AAAGAGAGTT       1200
TGGCGGCGCA   AGATGGTTTG   TGGAGGGAGA   TATAAAAGGC   TGCTTCGATA   ATATAGACCA       1260
CGTTACACTC   ATTGGACTCA   TCAATCTTAA   AATCAAAGAT   ATGAAAATGA   GCCAATTGAT       1320
TTATAAATTT   CTAAAAGCAG   GTTATCTGGA   AAACTGGCAG   TATCACAAAA   CTTACAGCGG       1380
AACACCTCAA   GGTGGAATTC   TATCTCCTCT   TTTGGCCAAC   ATCTATCTTC   ATGAATTGGA       1440
TAAGTTTGTT   TTACAACTCA   AAATGAAGTT   TGACCGAGAA   AGTCCAGAAA   GAATAACACC       1500
TGAATATCGG   GAACTTCACA   ATGAGATAAA   AGAATTTCT    CACCGTCTCA   AGAAGTTGGA       1560
GGGTGAAGAA   AAAGCTAAAG   TTCTTTTAGA   ATATCAAGAA   AAACGTAAAA   GATTACCCAC       1620
ACTCCCCTGT   ACCTCACAGA   CAAATAAAGT   ATTGAAATAC   GTCCGGTATG   CGGACGACTT       1680
CATTATCTCT   GTTAAAGGAA   GCAAAGAGGA   CTGTCAATGG   ATAAAAGAAC   AATTAAAACT       1740
TTTTATTCAT   AACAAGCTAA   AAATGGAATT   GAGTGAAGAA   AAAACACTCA   TCACACATAG       1800
```

-continued

| | | | | | |
|---|---|---|---|---|---|
| CAGTCAACCC | GCTCGTTTTC | TGGGATATGA | TATACGAGTA | AGGAGAAGTG | GAACGATAAA | 1860 |
| ACGATCTGGT | AAAGTCAAAA | AGAGAACACT | CAATGGGAGT | GTAGAACTCC | TTATTCCTCT | 1920 |
| TCAAGACAAA | ATTCGTCAAT | TTATTTTTGA | CAAGAAAATA | GCTATCCAAA | AGAAAGATAG | 1980 |
| CTCATGGTTT | CCAGTTCACA | GGAAATATCT | TATTCGTTCA | ACAGACTTAG | AAATCATCAC | 2040 |
| AATTTATAAT | TCTGAATTAA | GAGGGATTTG | TAATTACTAC | GGTCTAGCAA | GTAATTTAA | 2100 |
| CCAGCTCAAT | TATTTTGCTT | ATCTTATGGA | ATACAGCTGT | CTAAAAACGA | TAGCCTCCAA | 2160 |
| ACATAAGGGA | ACACTTTCAA | AAACCATTTC | CATGTTTAAA | GATGGAAGTG | GTTCGTGGGG | 2220 |
| CATCCCGTAT | GAGATAAAGC | AAGGTAAGCA | GCGCCGTTAT | TTTGCAAATT | TTAGTGAATG | 2280 |
| TAAATCCCCT | TATCAATTTA | CGGATGAGAT | AAGTCAAGCT | CCTGTATTGT | ATGGCTATGC | 2340 |
| CCGGAATACT | CTTGAAAACA | GGTTAAAAGC | TAAATGTTGT | GAATTATGTG | AACATCTGA | 2400 |
| TGAAAATACT | TCCTATGAAA | TTCACCATGT | CAATAAGGTC | AAAAATCTTA | AAGGCAAAGA | 2460 |
| AAAATGGGAA | ATGGCAATGA | TAGCGAAACA | ACGTAAAACT | CTTGTTGTAT | GCTTTCATTG | 2520 |
| TCATCGTCAC | GTGATTCATA | AACACAAGTG | AATTTTTACG | AACGAACAAT | AACAGAGCCG | 2580 |
| TATACTCCGA | GAGGGGTACG | TACGGTTCCC | GAAGAGGGTG | GTGCAAACCA | GTCACAGTAA | 2640 |
| TGTGAACAAG | GCGGTACCTC | CCTACTTCAC | CATATCATTT | TTAATTCTAC | GAATCTTTAT | 2700 |
| ACTGGCAAAC | AATTTGACTG | GAAAGTCATT | CCTAAAGAGA | AAACAAAAAG | CGGCAAAGCT | 2760 |
| T | | | | | | 2761 |

( 2 ) INFORMATION FOR SEQ ID NO:2:

( i ) SEQUENCE CHARACTERISTICS:
        ( A ) LENGTH: 1800 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1800

( x i ) SEQUENCE DESCRIPTION: SEQ ID NO:2:

```
ATG   AAA   CCA   ACA   ATG   GCA   ATT   TTA   GAA   AGA   ATC   AGT   AAA   AAT   TCA   CAA        48
Met   Lys   Pro   Thr   Met   Ala   Ile   Leu   Glu   Arg   Ile   Ser   Lys   Asn   Ser   Gln
 1                      5                         10                        15

GAA   AAT   ATA   GAC   GAA   GTT   TTT   ACA   AGA   CTT   TAT   CGT   TAT   CTT   TTA   CGT        96
Glu   Asn   Ile   Asp   Glu   Val   Phe   Thr   Arg   Leu   Tyr   Arg   Tyr   Leu   Leu   Arg
                  20                        25                        30

CCA   GAT   ATT   TAT   TAC   GTG   GCG   TAT   CAA   AAT   TTA   TAT   TCC   AAT   AAA   GGA       144
Pro   Asp   Ile   Tyr   Tyr   Val   Ala   Tyr   Gln   Asn   Leu   Tyr   Ser   Asn   Lys   Gly
            35                        40                        45

GCT   TCC   ACA   AAA   GGA   ATA   TTA   GAT   GAT   ACA   GCG   GAT   GGC   TTT   AGT   GAA       192
Ala   Ser   Thr   Lys   Gly   Ile   Leu   Asp   Asp   Thr   Ala   Asp   Gly   Phe   Ser   Glu
      50                        55                        60

GAA   AAA   ATA   AAA   AAG   ATT   ATT   CAA   TCT   TTA   AAA   GAC   GGA   ACT   TAC   TAT       240
Glu   Lys   Ile   Lys   Lys   Ile   Ile   Gln   Ser   Leu   Lys   Asp   Gly   Thr   Tyr   Tyr
65                        70                        75                        80

CCT   CAA   CCT   GTA   CGA   AGA   ATG   TAT   ATT   GCA   AAA   AAG   AAT   TCT   AAA   AAG       288
Pro   Gln   Pro   Val   Arg   Arg   Met   Tyr   Ile   Ala   Lys   Lys   Asn   Ser   Lys   Lys
                        85                        90                        95

ATG   AGA   CCT   TTA   GGA   ATT   CCA   ACT   TTC   ACA   GAT   AAA   TTG   ATC   CAA   GAA       336
Met   Arg   Pro   Leu   Gly   Ile   Pro   Thr   Phe   Thr   Asp   Lys   Leu   Ile   Gln   Glu
                  100                       105                       110

GCT   GTG   AGA   ATA   ATT   CTT   GAA   TCT   ATC   TAT   GAA   CCG   GTA   TTC   GAA   GAT       384
```

```
Ala Val Arg Ile Ile Leu Glu Ser Ile Tyr Glu Pro Val Phe Glu Asp
        115             120             125

GTG TCT CAC GGT TTT AGA CCT CAA CGA AGC TGT CAC ACA GCT TTG AAA      432
Val Ser His Gly Phe Arg Pro Gln Arg Ser Cys His Thr Ala Leu Lys
    130             135             140

ACA ATC AAA AGA GAG TTT GGC GGC GCA AGA TGG TTT GTG GAG GGA GAT      480
Thr Ile Lys Arg Glu Phe Gly Gly Ala Arg Trp Phe Val Glu Gly Asp
145             150             155             160

ATA AAA GGC TGC TTC GAT AAT ATA GAC CAC GTT ACA CTC ATT GGA CTC      528
Ile Lys Gly Cys Phe Asp Asn Ile Asp His Val Thr Leu Ile Gly Leu
                165             170             175

ATC AAT CTT AAA ATC AAA GAT ATG AAA ATG AGC CAA TTG ATT TAT AAA      576
Ile Asn Leu Lys Ile Lys Asp Met Lys Met Ser Gln Leu Ile Tyr Lys
        180             185             190

TTT CTA AAA GCA GGT TAT CTG GAA AAC TGG CAG TAT CAC AAA ACT TAC      624
Phe Leu Lys Ala Gly Tyr Leu Glu Asn Trp Gln Tyr His Lys Thr Tyr
        195             200             205

AGC GGA ACA CCT CAA GGT GGA ATT CTA TCT CCT CTT TTG GCC AAC ATC      672
Ser Gly Thr Pro Gln Gly Gly Ile Leu Ser Pro Leu Leu Ala Asn Ile
    210             215             220

TAT CTT CAT GAA TTG GAT AAG TTT GTT TTA CAA CTC AAA ATG AAG TTT      720
Tyr Leu His Glu Leu Asp Lys Phe Val Leu Gln Leu Lys Met Lys Phe
225             230             235             240

GAC CGA GAA AGT CCA GAA AGA ATA ACA CCT GAA TAT CGG GAA CTT CAC      768
Asp Arg Glu Ser Pro Glu Arg Ile Thr Pro Glu Tyr Arg Glu Leu His
                245             250             255

AAT GAG ATA AAA AGA ATT TCT CAC CGT CTC AAG AAG TTG GAG GGT GAA      816
Asn Glu Ile Lys Arg Ile Ser His Arg Leu Lys Lys Leu Glu Gly Glu
        260             265             270

GAA AAA GCT AAA GTT CTT TTA GAA TAT CAA GAA AAA CGT AAA AGA TTA      864
Glu Lys Ala Lys Val Leu Leu Glu Tyr Gln Glu Lys Arg Lys Arg Leu
        275             280             285

CCC ACA CTC CCC TGT ACC TCA CAG ACA AAT AAA GTA TTG AAA TAC GTC      912
Pro Thr Leu Pro Cys Thr Ser Gln Thr Asn Lys Val Leu Lys Tyr Val
    290             295             300

CGG TAT GCG GAC GAC TTC ATT ATC TCT GTT AAA GGA AGC AAA GAG GAC      960
Arg Tyr Ala Asp Asp Phe Ile Ile Ser Val Lys Gly Ser Lys Glu Asp
305             310             315             320

TGT CAA TGG ATA AAA GAA CAA TTA AAA CTT TTT ATT CAT AAC AAG CTA     1008
Cys Gln Trp Ile Lys Glu Gln Leu Lys Leu Phe Ile His Asn Lys Leu
                325             330             335

AAA ATG GAA TTG AGT GAA GAA AAA ACA CTC ATC ACA CAT AGC AGT CAA     1056
Lys Met Glu Leu Ser Glu Glu Lys Thr Leu Ile Thr His Ser Ser Gln
        340             345             350

CCC GCT CGT TTT CTG GGA TAT GAT ATA CGA GTA AGG AGA AGT GGA ACG     1104
Pro Ala Arg Phe Leu Gly Tyr Asp Ile Arg Val Arg Arg Ser Gly Thr
    355             360             365

ATA AAA CGA TCT GGT AAA GTC AAA AAG AGA ACA CTC AAT GGG AGT GTA     1152
Ile Lys Arg Ser Gly Lys Val Lys Lys Arg Thr Leu Asn Gly Ser Val
370             375             380

GAA CTC CTT ATT CCT CTT CAA GAC AAA ATT CGT CAA TTT ATT TTT GAC     1200
Glu Leu Leu Ile Pro Leu Gln Asp Lys Ile Arg Gln Phe Ile Phe Asp
385             390             395             400

AAG AAA ATA GCT ATC CAA AAG AAA GAT AGC TCA TGG TTT CCA GTT CAC     1248
Lys Lys Ile Ala Ile Gln Lys Lys Asp Ser Ser Trp Phe Pro Val His
                405             410             415

AGG AAA TAT CTT ATT CGT TCA ACA GAC TTA GAA ATC ATC ACA ATT TAT     1296
Arg Lys Tyr Leu Ile Arg Ser Thr Asp Leu Glu Ile Ile Thr Ile Tyr
        420             425             430

AAT TCT GAA TTA AGA GGG ATT TGT AAT TAC TAC GGT CTA GCA AGT AAT     1344
```

```
                    Asn  Ser  Glu  Leu  Arg  Gly  Ile  Cys  Asn  Tyr  Tyr  Gly  Leu  Ala  Ser  Asn
                              435                      440                      445

TTT  AAC  CAG  CTC  AAT  TAT  TTT  GCT  TAT  CTT  ATG  GAA  TAC  AGC  TGT  CTA                          1392
Phe  Asn  Gln  Leu  Asn  Tyr  Phe  Ala  Tyr  Leu  Met  Glu  Tyr  Ser  Cys  Leu
     450                      455                      460

AAA  ACG  ATA  GCC  TCC  AAA  CAT  AAG  GGA  ACA  CTT  TCA  AAA  ACC  ATT  TCC                          1440
Lys  Thr  Ile  Ala  Ser  Lys  His  Lys  Gly  Thr  Leu  Ser  Lys  Thr  Ile  Ser
465                      470                      475                      480

ATG  TTT  AAA  GAT  GGA  AGT  GGT  TCG  TGG  GGC  ATC  CCG  TAT  GAG  ATA  AAG                          1488
Met  Phe  Lys  Asp  Gly  Ser  Gly  Ser  Trp  Gly  Ile  Pro  Tyr  Glu  Ile  Lys
                         485                      490                      495

CAA  GGT  AAG  CAG  CGC  CGT  TAT  TTT  GCA  AAT  TTT  AGT  GAA  TGT  AAA  TCC                          1536
Gln  Gly  Lys  Gln  Arg  Arg  Tyr  Phe  Ala  Asn  Phe  Ser  Glu  Cys  Lys  Ser
               500                      505                      510

CCT  TAT  CAA  TTT  ACG  GAT  GAG  ATA  AGT  CAA  GCT  CCT  GTA  TTG  TAT  GGC                          1584
Pro  Tyr  Gln  Phe  Thr  Asp  Glu  Ile  Ser  Gln  Ala  Pro  Val  Leu  Tyr  Gly
          515                      520                      525

TAT  GCC  CGG  AAT  ACT  CTT  GAA  AAC  AGG  TTA  AAA  GCT  AAA  TGT  TGT  GAA                          1632
Tyr  Ala  Arg  Asn  Thr  Leu  Glu  Asn  Arg  Leu  Lys  Ala  Lys  Cys  Cys  Glu
     530                      535                      540

TTA  TGT  GGA  ACA  TCT  GAT  GAA  AAT  ACT  TCC  TAT  GAA  ATT  CAC  CAT  GTC                          1680
Leu  Cys  Gly  Thr  Ser  Asp  Glu  Asn  Thr  Ser  Tyr  Glu  Ile  His  His  Val
545                      550                      555                      560

AAT  AAG  GTC  AAA  AAT  CTT  AAA  GGC  AAA  GAA  AAA  TGG  GAA  ATG  GCA  ATG                          1728
Asn  Lys  Val  Lys  Asn  Leu  Lys  Gly  Lys  Glu  Lys  Trp  Glu  Met  Ala  Met
                         565                      570                      575

ATA  GCG  AAA  CAA  CGT  AAA  ACT  CTT  GTT  GTA  TGC  TTT  CAT  TGT  CAT  CGT                          1776
Ile  Ala  Lys  Gln  Arg  Lys  Thr  Leu  Val  Val  Cys  Phe  His  Cys  His  Arg
               580                      585                      590

CAC  GTG  ATT  CAT  AAA  CAC  AAG  TGA                                                                   1800
His  Val  Ile  His  Lys  His  Lys   *
          595                      600
```

( 2 ) INFORMATION FOR SEQ ID NO:3:

( i ) SEQUENCE CHARACTERISTICS:
        ( A ) LENGTH: 599 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Lys  Pro  Thr  Met  Ala  Ile  Leu  Glu  Arg  Ile  Ser  Lys  Asn  Ser  Gln
 1                    5                        10                       15

Glu  Asn  Ile  Asp  Glu  Val  Phe  Thr  Arg  Leu  Tyr  Arg  Tyr  Leu  Leu  Arg
               20                       25                       30

Pro  Asp  Ile  Tyr  Tyr  Val  Ala  Tyr  Gln  Asn  Leu  Tyr  Ser  Asn  Lys  Gly
          35                       40                       45

Ala  Ser  Thr  Lys  Gly  Ile  Leu  Asp  Asp  Thr  Ala  Asp  Gly  Phe  Ser  Glu
     50                       55                       60

Glu  Lys  Ile  Lys  Lys  Ile  Ile  Gln  Ser  Leu  Lys  Asp  Gly  Thr  Tyr  Tyr
65                       70                       75                       80

Pro  Gln  Pro  Val  Arg  Arg  Met  Tyr  Ile  Ala  Lys  Lys  Asn  Ser  Lys  Lys
               85                       90                       95

Met  Arg  Pro  Leu  Gly  Ile  Pro  Thr  Phe  Thr  Asp  Lys  Leu  Ile  Gln  Glu
               100                      105                      110

Ala  Val  Arg  Ile  Ile  Leu  Glu  Ser  Ile  Tyr  Glu  Pro  Val  Phe  Glu  Asp
          115                      120                      125

Val  Ser  His  Gly  Phe  Arg  Pro  Gln  Arg  Ser  Cys  His  Thr  Ala  Leu  Lys
```

-continued

```
            130                          135                           140

Thr  Ile  Lys  Arg  Glu  Phe  Gly  Gly  Ala  Arg  Trp  Phe  Val  Glu  Gly  Asp
145                      150                         155                    160

Ile  Lys  Gly  Cys  Phe  Asp  Asn  Ile  Asp  His  Val  Thr  Leu  Ile  Gly  Leu
                165                      170                    175

Ile  Asn  Leu  Lys  Ile  Lys  Asp  Met  Lys  Met  Ser  Gln  Leu  Ile  Tyr  Lys
                180                 185                              190

Phe  Leu  Lys  Ala  Gly  Tyr  Leu  Glu  Asn  Trp  Gln  Tyr  His  Lys  Thr  Tyr
           195                 200                         205

Ser  Gly  Thr  Pro  Gln  Gly  Gly  Ile  Leu  Ser  Pro  Leu  Leu  Ala  Asn  Ile
     210                 215                         220

Tyr  Leu  His  Glu  Leu  Asp  Lys  Phe  Val  Leu  Gln  Leu  Lys  Met  Lys  Phe
225                      230                      235                         240

Asp  Arg  Glu  Ser  Pro  Glu  Arg  Ile  Thr  Pro  Glu  Tyr  Arg  Glu  Leu  His
                245                      250                              255

Asn  Glu  Ile  Lys  Arg  Ile  Ser  His  Arg  Leu  Lys  Lys  Leu  Glu  Gly  Glu
                260                 265                         270

Glu  Lys  Ala  Lys  Val  Leu  Leu  Glu  Tyr  Gln  Glu  Lys  Arg  Lys  Arg  Leu
           275                      280                    285

Pro  Thr  Leu  Pro  Cys  Thr  Ser  Gln  Thr  Asn  Lys  Val  Leu  Lys  Tyr  Val
     290                      295                    300

Arg  Tyr  Ala  Asp  Asp  Phe  Ile  Ile  Ser  Val  Lys  Gly  Ser  Lys  Glu  Asp
305                      310                    315                         320

Cys  Gln  Trp  Ile  Lys  Glu  Gln  Leu  Lys  Leu  Phe  Ile  His  Asn  Lys  Leu
                325                      330                         335

Lys  Met  Glu  Leu  Ser  Glu  Glu  Lys  Thr  Leu  Ile  Thr  His  Ser  Ser  Gln
                340                 345                         350

Pro  Ala  Arg  Phe  Leu  Gly  Tyr  Asp  Ile  Arg  Val  Arg  Arg  Ser  Gly  Thr
           355                 360                         365

Ile  Lys  Arg  Ser  Gly  Lys  Val  Lys  Lys  Arg  Thr  Leu  Asn  Gly  Ser  Val
     370                 375                    380

Glu  Leu  Leu  Ile  Pro  Leu  Gln  Asp  Lys  Ile  Arg  Gln  Phe  Ile  Phe  Asp
385                 390                    395                              400

Lys  Lys  Ile  Ala  Ile  Gln  Lys  Lys  Asp  Ser  Ser  Trp  Phe  Pro  Val  His
                405                 410                         415

Arg  Lys  Tyr  Leu  Ile  Arg  Ser  Thr  Asp  Leu  Glu  Ile  Ile  Thr  Ile  Tyr
           420                 425                         430

Asn  Ser  Glu  Leu  Arg  Gly  Ile  Cys  Asn  Tyr  Tyr  Gly  Leu  Ala  Ser  Asn
           435                 440                         445

Phe  Asn  Gln  Leu  Asn  Tyr  Phe  Ala  Tyr  Leu  Met  Glu  Tyr  Ser  Cys  Leu
     450                 455                         460

Lys  Thr  Ile  Ala  Ser  Lys  His  Lys  Gly  Thr  Leu  Ser  Lys  Thr  Ile  Ser
465                      470                    475                         480

Met  Phe  Lys  Asp  Gly  Ser  Gly  Ser  Trp  Gly  Ile  Pro  Tyr  Glu  Ile  Lys
                485                      490                         495

Gln  Gly  Lys  Gln  Arg  Arg  Tyr  Phe  Ala  Asn  Phe  Ser  Glu  Cys  Lys  Ser
                500                 505                         510

Pro  Tyr  Gln  Phe  Thr  Asp  Glu  Ile  Ser  Gln  Ala  Pro  Val  Leu  Tyr  Gly
           515                 520                    525

Tyr  Ala  Arg  Asn  Thr  Leu  Glu  Asn  Arg  Leu  Lys  Ala  Lys  Cys  Cys  Glu
     530                 535                    540

Leu  Cys  Gly  Thr  Ser  Asp  Glu  Asn  Thr  Ser  Tyr  Glu  Ile  His  His  Val
545                 550                    555                              560
```

| Asn | Lys | Val | Lys | Asn | Leu | Lys | Gly | Lys | Glu | Lys | Trp | Glu | Met | Ala | Met |
|-----|-----|-----|-----|-----|-----|-----|-----|-----|-----|-----|-----|-----|-----|-----|-----|
|     |     |     |     | 565 |     |     |     |     | 570 |     |     |     |     | 575 |     |

| Ile | Ala | Lys | Gln | Arg | Lys | Thr | Leu | Val | Val | Cys | Phe | His | Cys | His | Arg |
|-----|-----|-----|-----|-----|-----|-----|-----|-----|-----|-----|-----|-----|-----|-----|-----|
|     |     |     |     | 580 |     |     |     | 585 |     |     |     |     | 590 |     |     |

| His | Val | Ile | His | Lys | His | Lys |
|-----|-----|-----|-----|-----|-----|-----|
|     |     |     |     | 595 |     |     | 600 |

( 2 ) INFORMATION FOR SEQ ID NO:4:

( i ) SEQUENCE CHARACTERISTICS:
        ( A ) LENGTH: 129 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

| CGCTCTAGAA | CTAGTGGATC | CTTGCAACCC | ACGTCGATCG | TGAACACATC | CATAACCATA | 60 |
| TCATTTTTAA | TTCTACGAAT | CTTTATACTG | GGAATTCGAT | ATCAAGCTTA | TCGATACCGT | 120 |
| CGACCTCGA | | | | | | 129 |

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TCTACCTCAT CTAGACATTT TCTCC     25

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CGTTCGTAAA GCTAGCCTTG TGTTTATG     28

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CACAAAGTGA TCATTTAACG AACG     24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single -continued (D) TOPOLOGY: linear (ii) MOLECULE TYPE: DNA (genomic)

(xi) SEQUENCE DESCRIPTION: SEQ ID NO:8:

TTGGGATCCT CATAAGCTTT GCCGC 25

(2) INFORMATION FOR SEQ ID NO:9:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

CAAAGGATCC GATGAAACCA ACAATGGCAA 30

(2) INFORMATION FOR SEQ ID NO:10:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

AGTGGCTTCC ATATGCTTGG TCATCACCTC ATC 33

(2) INFORMATION FOR SEQ ID NO:11:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GGTAGAACCA TATGAAATTC CTCCTCCCTA ATCAATTTT 39

(2) INFORMATION FOR SEQ ID NO:12:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

AAAACCTCCA TATGAAACCA ACAATG 26